United States Patent
Yang et al.

(10) Patent No.: US 9,822,420 B2
(45) Date of Patent: *Nov. 21, 2017

(54) METHOD OF SEPARATING CARBOHYDRATE

(71) Applicant: INDUSTRIAL TECHNOLOGY RESEARCH INSTITUTE, Chutung, Hsinchu (TW)

(72) Inventors: Tzu-Yueh Yang, Zhudong Township (TW); Ruey-Fu Shih, New Taipei (TW); Chih-Hao Chen, Hsinchu (TW); Hou-Peng Wan, Guishan Township (TW); Hom-Ti Lee, Zhubei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 85 days.

This patent is subject to a terminal disclaimer.

(21) Appl. No.: 14/198,914

(22) Filed: Mar. 6, 2014

(65) Prior Publication Data

US 2014/0261397 A1 Sep. 18, 2014

Related U.S. Application Data

(60) Provisional application No. 61/802,867, filed on Mar. 18, 2013.

(30) Foreign Application Priority Data

Nov. 21, 2013 (TW) .............................. 102142397 A

(51) Int. Cl.
| | |
|---|---|
| C13K 1/04 | (2006.01) |
| C07H 1/08 | (2006.01) |
| C07H 3/02 | (2006.01) |
| C13K 1/02 | (2006.01) |
| C13K 13/00 | (2006.01) |

(52) U.S. Cl.
CPC ................ *C13K 1/04* (2013.01); *C07H 1/08* (2013.01); *C07H 3/02* (2013.01); *C13K 1/02* (2013.01); *C13K 13/002* (2013.01)

(58) Field of Classification Search
CPC ...................................................... C13K 1/04
See application file for complete search history.

(56) References Cited

U.S. PATENT DOCUMENTS

| | | | | |
|---|---|---|---|---|
| 1,547,893 | A * | 7/1925 | Bergius | .................... C07C 17/38 127/37 |
| 4,018,620 | A * | 4/1977 | Penque | .................... C13K 1/02 127/37 |
| 4,452,640 | A | 6/1984 | Chen et al. | |
| 4,713,118 | A * | 12/1987 | Barker | .................... C13K 1/06 127/36 |
| 5,366,558 | A * | 11/1994 | Brink | ...................... B02C 13/18 127/37 |
| 5,538,637 | A | 7/1996 | Hester et al. | |
| 5,820,687 | A | 10/1998 | Farone et al. | |
| 6,007,636 | A * | 12/1999 | Lightner | .................. C08B 15/02 127/37 |
| 6,262,313 | B1 | 7/2001 | Holtzapple et al. | |
| 6,419,828 | B1 | 7/2002 | Russo, Jr. | |
| 6,423,145 | B1 * | 7/2002 | Nguyen | .................... C12P 7/08 106/164.5 |
| 8,003,352 | B2 | 8/2011 | Foody et al. | |
| 2002/0038058 | A1 | 3/2002 | Holtzapple et al. | |
| 2009/0023187 | A1 | 1/2009 | Foody et al. | |
| 2009/0253175 | A1 | 10/2009 | Bookbinder et al. | |
| 2010/0268000 | A1 | 10/2010 | Parekh et al. | |
| 2011/0180062 | A1 | 7/2011 | Takeshima et al. | |
| 2012/0227733 | A1 | 9/2012 | Eyal et al. | |
| 2012/0301948 | A1 | 11/2012 | Brennan et al. | |
| 2012/0323053 | A1 * | 12/2012 | Qiao | ........................ C10G 1/06 568/959 |
| 2014/0090641 | A1 | 4/2014 | Shih et al. | |

(Continued)

FOREIGN PATENT DOCUMENTS

| | | |
|---|---|---|
| CN | 101023179 A | 8/2007 |
| CN | 101285106 A | 10/2008 |

(Continued)

OTHER PUBLICATIONS

Simulated Moving Bed Chromatography (SMB) for Application in Bioseparatoin Sabine Imamoglu Advances in Biochemical Engineering/Biotechnology, vol. 76 pp. 211-231, 2002.*
Understanding Ion-Exchange Resins for Water Treatment Systems GE Water and Process Technologies, Technical Paper W.S. Miller et al. pp. 1-13, 1981.*
Some New Solvents for Cellulose and Their Action on this Substance Horace Deming Journal of the American Chemical Society vol. 33, pp. 1515-1525, 1911.*

(Continued)

*Primary Examiner* — Douglas B Call

(74) *Attorney, Agent, or Firm* — Birch, Stewart, Kolasch & Birch, LLP

(57) ABSTRACT

Disclosed is a method of separating carbohydrate, including: mixing formic acid with heteropoly acid, chloride or bromide of lithium, magnesium, calcium, zinc, or iron, or combinations thereof to form a mixing liquid. The method also includes dissolving a cellulose biomass by the mixing liquid to form a solution, mixing water and the solution to hydrolyze the cellulose biomass for forming a carbohydrate solution, and mixing an extractant and the carbohydrate solution to extract the formic acid out of the carbohydrate solution. The heteropoly acid, the chloride or bromide of lithium, magnesium, calcium, zinc, or iron, or combinations thereof in the carbohydrate solution is separated out of the carbohydrate solution by ion exclusion chromatography separation to obtain a carbohydrate.

17 Claims, 5 Drawing Sheets

(56) References Cited

U.S. PATENT DOCUMENTS

| | | | | |
|---|---|---|---|---|
| 2014/0093920 A1* | 4/2014 | Zhang | .................. | C08H 8/00 435/105 |
| 2014/0331992 A1* | 11/2014 | Tschentscher | ........... | C13K 1/02 127/34 |

FOREIGN PATENT DOCUMENTS

| | | |
|---|---|---|
| CN | 102026953 A | 4/2011 |
| CN | 102070571 A | 5/2011 |
| CN | 102174754 A | 9/2011 |
| CN | 102392082 A | 3/2012 |
| CN | 102600640 A | 7/2012 |
| CN | 102603504 A | 7/2012 |
| CN | 102690899 A | 9/2012 |
| CN | 102766703 A | 11/2012 |
| CN | 103710471 A | 4/2014 |
| EP | 0 151 671 A1 | 8/1985 |
| EP | 2 336 195 A1 | 6/2011 |
| GB | 311695 | 12/1929 |
| JP | 2005-239979 A | 9/2005 |
| JP | 2006-75007 A | 3/2006 |
| JP | 2009-291143 A | 12/2009 |
| JP | 2009-291145 A | 12/2009 |
| JP | 2011-101608 A | 5/2011 |
| JP | 2011-157225 A | 8/2011 |
| JP | 2011-168651 A | 9/2011 |
| NZ | 502461 A | 3/2002 |
| RU | 2 159 816 C2 | 11/2000 |
| TW | 360629 | 6/1999 |
| TW | 589320 | 6/2004 |
| TW | 237026 I | 8/2005 |
| WO | WO 95/17517 A1 | 6/1995 |
| WO | WO 96/40970 A1 | 12/1996 |
| WO | WO 02/02826 A1 | 1/2002 |
| WO | WO 2006/007691 A1 | 1/2006 |
| WO | WO 2009/031469 A1 | 3/2009 |
| WO | WO 2009/130387 A2 | 10/2009 |
| WO | WO 2011/002660 A1 | 1/2011 |
| WO | WO 2012/168410 | * 12/2012 |
| WO | WO2013110814 | * 8/2013 |

OTHER PUBLICATIONS

Inorganic molten salts as solvents for cellulose S. Fischer et al. Cellulose, vol. 10, pp. 227-236, 2003.*

Switchgrass pretreatment and hydrolysis using low concentrations of formic acid T. Marzialetti et al. j Chem Technol Biotechnol V. 86, pp. 706-713, 2011.*

European Search Report, dated Jun. 17, 2014, for European Application No. 14160327.4.

China Office Action dated Jun. 16, 2015 for Appl. No. 201410004830.1.

Binder et al., "Fermentable sugars by chemical hydrolysis of biomass," PNAS, Mar. 9, 2010, vol. 107, No. 10, pp. 4516-4521.

Mai et al., "Recovery of ionic liquid and sugars from hydrolyzed biomass using ion exclusion simulated moving bed chromatography," Journal of Chromatography A, 2012, vol. 1227, pp. 67-72.

Nam et al., "Comparison of Amberchrom-CG161C and Dowex99 as the adsorbent of a four-zone simulated moving bed process for removal of acetic acid from biomass hydrolyzate," Process Biochemistry, 2011, vol. 46, pp. 2044-2053.

Nam et al., "Optimal design and experimental validation of a three-zone simulated moving bed process based on the Amberchrom-CG161C adsorbent for continuous removal of acetic acid from biomass hydrolyzate," Process Biochemistry, 2012, vol. 47, pp. 725-734.

Sun et al., "Production of fuel ethanol from bamboo by concentrated sulfuric acid hydrolysis followed by continuous ethanol fermentation," Bioresource Technology, 2011, vol. 102, pp. 10929-10935.

Taiwanese Office Action dated Oct. 9, 2014, issued in corresponding Taiwanese Patent Application No. 10321410770.

* cited by examiner

METHOD OF SEPARATING CARBOHYDRATE

CROSS REFERENCE TO RELATED APPLICATIONS

This application claims the benefit of U.S. Provisional Application No. 61/802,867, filed on Mar. 18, 2013, and claims priority of Taiwan Application Serial Number 102142397, filed on Nov. 21, 2013, the disclosure of which are hereby incorporated by reference herein in its entirety.

TECHNICAL FIELD

The technical field relates to a method of separating a carbohydrate.

BACKGROUND

The world is facing problems such as the gradual extraction and depletion of petroleum reserves, and changes to the earth's atmosphere due to the greenhouse effect. In order to ensure the sustainability of human life, it has become a world trend to gradually decrease the use of petrochemical energy and petroleum feedstock and to develop new sources of renewable energy and materials.

Lignocellulose is the main ingredient of biomass, which is the most abundant organic substance in the world. Lignocellulose mainly consists of 38-50% cellulose, 23-32% hemicellulose, and 15-25% lignin. The cellulose can be hydrolyzed to form glucose. However, it is difficult for chemicals to enter the interior of cellulose molecules for depolymerization due to strong intermolecular and intramolecular hydrogen bonding and Van de Waal forces, complex aggregation, and high crystallinity of the cellulose. The main hydrolysis methods for the cellulose are enzyme hydrolysis and acid hydrolysis. However, these two technologies have obvious defects hampering their wide application.

In general, the enzyme hydrolysis can be carried out at room temperature, which is an environmentally friendly method due to rare byproducts, no production of anti-carbohydrate fermentation substances, and integration with the fermentation process. However, a complicated pretreatment process is required for the enzyme hydrolysis. In addition, hydrolytic activity is low, the reaction rate is slow, and cellulose hydrolysis enzyme is expensive. Dilute acid hydrolysis generally uses comparatively cheap sulfuric acid as a catalyst, but it must operate in a corrosion-resistant pressure vessel at a temperature greater than 200° C., thereby requiring high-level equipment. Simultaneously, the temperature of the dilute acid hydrolysis is high, the byproduct thereof is plentiful, and the carbohydrate yield is low. Concentrated acid hydrolysis can be operated at a lower temperature and a normal pressure. However, the concentrated acid hydrolysis has problems such as strong corrosivity from concentrated acid, a complex post-treatment process of the hydrolyzed solution, large consumption of acid, and difficulties for recycling, and the likes.

Accordingly, a novel method to hydrolyze the cellulose biomass is called-for.

SUMMARY

One embodiment of the disclosure provides a method of separating carbohydrate, comprising: mixing formic acid with heteropoly acid, chloride or bromide of lithium, magnesium, calcium, zinc, or iron, or combinations thereof to form a mixing liquid, dissolving a cellulose biomass by the mixing liquid to form a solution; mixing water and the solution to hydrolyze the cellulose biomass for forming a carbohydrate solution; mixing an extractant and the carbohydrate solution to extract the formic acid out of the carbohydrate solution; and separating the heteropoly acid, the chloride or bromide of lithium, magnesium, calcium, zinc, or iron, or combinations thereof out of the carbohydrate solution by an ion exclusion chromatography separation to obtain a carbohydrate.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
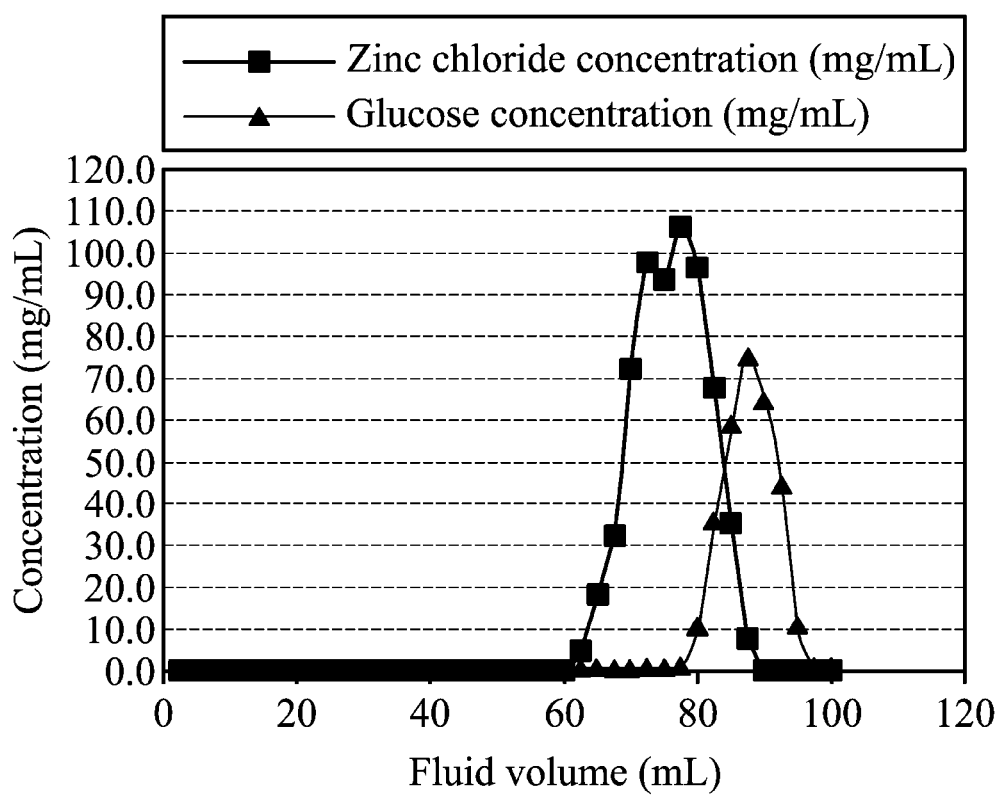
FIG. 1 shows curves of glucose concentration and zinc ion concentration versus fluid volume of a fluid that flowed out of a zinc ion exchanged cationic resin for separating glucose and zinc ions in one embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment, a method of separating carbohydrate is disclosed. Formic acid is firstly mixed with a polyhetero acid, a chloride or bromide of lithium, magnesium, calcium, zinc, or iron, or combinations thereof to form a mixing liquid. A cellulose biomass is then dissolved by the mixing liquid to from a solution. Subsequently, the solution and water are mixed to hydrolyze the cellulose biomass for forming a carbohydrate solution. The formic acid in the mixing liquid has a concentration of about 60 wt % to 99 wt %.

In one embodiment, the mixing liquid includes the formic acid and the heteropoly acid. In another embodiment, the mixing liquid includes the formic acid and the chloride or bromide of lithium, magnesium, calcium, zinc, or iron. In other embodiments, the mixing liquid includes the formic acid, the chloride or bromide, and the heteropoly acid.

The heteropoly acid can be $H_3PW_{12}O_{40}$, $H_4SiW_{12}O_{40}$, $H_3PMo_{12}O_{40}$, $H_4SiMo_{12}O_{40}$, or combinations thereof. In one embodiment of the disclosure, the heteropoly acid in the mixing liquid has a concentration of 1 wt % to 5 wt %, or of 2 wt % to 5 wt %.

In one embodiment, the lithium chloride or the lithium bromide in the mixing liquid has a concentration of about 5 wt % to 20 wt %, or of about 10 wt % to 20 wt %. In one embodiment, the magnesium chloride or the magnesium bromide in the mixing liquid has a concentration of about 10 wt % to 30 wt %, or of about 15 wt % to 20 wt %. In one embodiment, the calcium chloride or the calcium bromide in the mixing liquid has a concentration of about 12 wt % to 40 wt %, or of about 12 wt % to 30 wt %. In one embodiment, the zinc chloride or the zinc bromide in the mixing liquid has a concentration of about 5 wt % to 45 wt %, or of about 20 wt % to 30 wt %. In one embodiment, the iron chloride or the iron bromide in the mixing liquid has a concentration of about 1 wt % to 50 wt %, or of about 5 wt % to 10 wt %.

The cellulose biomass source can be wood, grass, leaves, algae, waste paper, corn stalks, corn cobs, rice straw, rice husk, wheat straw, sugar cane bagasse, bamboo, or crop stems. The cellulose biomass may include lignocellulose, lignohemicellulose, or combinations thereof, and the cellulose biomass in the mixing liquid has a concentration of about 1 wt % to 20 wt %, or of about 5 wt % to 15 wt %.

The step of dissolving the cellulose biomass by the mixing liquid to form a solution can be performed at a temperature of about 40° C. to 90° C. (or of about 50° C. to 70° C.) for a period of about 20 minutes to 6 hours (or of about 30 minutes to 2 hours).

In the hydrolysis of the cellulose biomass for forming a carbohydrate solution, the water amount is greater than a total molar equivalent of the monosaccharide (hydrolyzed from the cellulose biomass). In one embodiment, the hydrolysis is performed at a temperature of about 50° C. to 150° C., or of about 60° C. to 105° C. In one embodiment, the hydrolysis is performed for a period of about 30 minutes to 3 hours, or of about 30 minutes to 2 hours.

In one embodiment, an inorganic acid is further added into the mixing liquid before dissolving the cellulose biomass by the mixing liquid. The inorganic acid can be sulfuric acid or hydrochloric acid. The inorganic acid in the mixing liquid has a concentration of about 1 wt % to 2 wt %. The inorganic acid may reduce the amount of the metal salt (such as metal chlorides and the metal bromides) in the mixing liquid. For example, the concentration of the magnesium chloride, the magnesium bromide, the calcium chloride, or the calcium bromide in the mixing liquid (including the inorganic acid) can be reduced to about 1 wt % to 10 wt %. The concentration of the lithium chloride, the lithium bromide, the zinc chloride, zinc bromide, iron chloride, or the iron bromide in the mixing liquid (including the inorganic acid) can be reduced to about 1 wt % to 5 wt %.

The mixing liquid of the formic acid (weak acid) with the heteropoly acid, the chloride or the bromide of lithium, magnesium, calcium, zinc, or iron, or combinations thereof can be used to dissolve the cellulose biomass at a low temperature (<90° C.) for a short period (<6 hours) to form a homogeneous solution. The method of dissolving and hydrolyzing the cellulose biomass to form the carbohydrate has properties such as low temperature and normal pressure, fast, high yield, and free of any strong-acid corrosion resistant reactor.

In one embodiment, the carbohydrate solution is optionally distilled to obtain an azeotropic distillate of water and a part of formic acid, thereby increasing the carbohydrate concentration of the carbohydrate solution. For example, the distillation can be performed at a temperature of 40° C. to 60° C. and under a pressure of 20 torr to 500 torr. A lower distillation pressure may cause a lower distillation temperature. The distilled formic acid can be further purified, and then reused in the described mixing liquid. In one embodiment, solids in the carbohydrate solution can be removed by centrifuge and/or filtration.

Thereafter, the carbohydrate solution and an extractant are mixed to extract the formic acid out of the carbohydrate solution. In one embodiment, the extractant and the carbohydrate solution has a volume ratio of 1:1 to 12:1. In one embodiment, the extractant can be tributyl phosphate, tri-n-octylphosphine oxide, trioctyl amine, diisobutyl ketone (DIBK), di(2-ethylhexly) phosphoric acid (D2EHPA), or combinations thereof. In one embodiment, precipitation is precipitated during the step of mixing the carbohydrate solution and the extractant, and the precipitation can be removed by centrifuge and/or filtration.

In one embodiment, the extractant and the formic acid can be separated by distillation after the step of extracting the formic acid out of the carbohydrate solution by the extractant. The distillation can be performed under a pressure of 20 torr to 760 torr and a temperature of 40° C. to 200° C.

In one embodiment, the azeotropic distillate of the water and the formic acid is mixed with the extract of the formic acid and the extractant (extracted from the carbohydrate solution) to form a mixture. The mixture is then heated to concentrate the formic acid. For example, the mixture is heated by a temperature of 50° C. to 105° C.

Subsequently, the heteropoly acid, the chloride or bromide of lithium, magnesium, calcium, zinc, or iron, or combinations thereof is separated out by an ion exclusion chromatography separation to obtain a carbohydrate. The ion exclusion chromatography separation means that the carbohydrate and the heteropoly acid, the chloride or bromide of lithium, magnesium, calcium, zinc, or iron, or combinations thereof is separated by an ionic exchange resin. If a cationic exchange resin is selected, cations (e.g. $H^+$, $Ca^{2+}$, $Na^+$, and the likes) of a cationic resin can be pre-exchanged by a metal salt solution of lithium, magnesium, calcium, zinc, or iron. If an anionic exchange resin is selected, anions (e.g. $OH^-$ or $Cl^-$) of an anionic resin can be pre-exchanged by a chloride or bromide solution.

The recycled formic acid, heteropoly acid, inorganic acid, and chloride or bromide of lithium, magnesium, calcium, zinc, or iron can be reused again to save raw material cost.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1-1

Formic acid and zinc chloride ($ZnCl_2$) were mixed and then heated to form a mixing liquid (60 wt % of the formic acid and 40 wt % of the zinc chloride). Avicel® cellulose (Avicel-pH-105-27NI, commercially available from Sigma Company) was added to the mixing liquid to be dissolved at 50° C. for 20 minutes. A yellow homogeneous transparent liquid with 15 wt % of the Avicel® cellulose was obtained, as tabulated in Table 1.

Example 1-2

Formic acid and zinc chloride (ZnCl$_2$) were mixed and then heated to form a mixing liquid (60 wt % of the formic acid and 40 wt % of the zinc chloride). α-cellulose (C8002, commercially available from Sigma Company) was added to the mixing liquid to be dissolved at 50° C. for 20 minutes. An amber homogeneous transparent liquid with 15 wt % of the α-cellulose was obtained, as tabulated in Table 1.

Example 1-3

Formic acid and calcium chloride (CaCl$_2$) were mixed and then heated to form a mixing liquid (75 wt % of the formic acid and 25 wt % of the calcium chloride). Avicel® cellulose (Avicel-pH-105-27NI, commercially available from Sigma Company) was added to the mixing liquid to be dissolved at 65° C. for 90 minutes. A yellow homogeneous transparent liquid with 6 wt % of the Avicel® cellulose was obtained, as tabulated in Table 1.

Example 1-4

Formic acid and calcium chloride (CaCl$_2$) were mixed and then heated to form a mixing liquid (75 wt % of the formic acid and 25 wt % of the calcium chloride). α-cellulose (C8002, commercially available from Sigma Company) was added to the mixing liquid to be dissolved at 65° C. for 90 minutes. An amber homogeneous transparent liquid with 6 wt % of the α-cellulose was obtained, as tabulated in Table 1.

Example 1-5

Formic acid and magnesium chloride (MgCl$_2$) were mixed and then heated to form a mixing liquid (80 wt % of the formic acid and 20 wt % of the magnesium chloride). Avicel® cellulose (Avicel-pH-105-27NI, commercially available from Sigma Company) was added to the mixing liquid to be dissolved at 65° C. for 120 minutes. An amber homogeneous transparent liquid with 5 wt % of the Avicel® cellulose was obtained, as tabulated in Table 1.

Example 1-6

Formic acid and magnesium chloride (MgCl$_2$) were mixed and then heated to form a mixing liquid (80 wt % of the formic acid and 20 wt % of the magnesium chloride). α-cellulose (C8002, commercially available from Sigma Company) was added to the mixing liquid to be dissolved at 65° C. for 120 minutes. An amber homogeneous transparent liquid with 5 wt % of the α-cellulose was obtained, as tabulated in Table 1.

TABLE 1

| Examples | Salt (wt %) | Cellulose (wt %) | Dissolving temperature (° C.) | Dissolving period (minutes) | Solution appearance |
|---|---|---|---|---|---|
| 1-1 | ZnCl$_2$ (40) | Avicel® cellulose (15) | 50 | 20 | Yellow homogeneous transparent liquid |
| 1-2 | ZnCl$_2$ (40) | α-cellulose (15) | 50 | 20 | Amber homogeneous transparent liquid |
| 1-3 | CaCl$_2$ (25) | Avicel® cellulose (6) | 65 | 90 | Yellow homogeneous transparent liquid |
| 1-4 | CaCl$_2$ (25) | α-cellulose (6) | 65 | 90 | Amber homogeneous transparent liquid |
| 1-5 | MgCl$_2$ (20) | Avicel® cellulose (5) | 65 | 120 | Amber homogeneous transparent liquid |
| 1-6 | MgCl$_2$ (20) | α-cellulose (5) | 65 | 120 | Amber homogeneous transparent liquid |

Example 2-1

Formic acid and lithium chloride (LiCl) were mixed and then heated to form a mixing liquid (90 wt % of the formic acid and 10 wt % of the lithium chloride). Avicel® cellulose (Avicel-pH-105-27NI, commercially available from Sigma Company) was added into the mixing liquid to form a mixture with 5 wt % of the Avicel® cellulose. The mixture stood at 70° C. for 6 hours to test its solubility. The cellulose solubility was observed by a polarizing microscope, and the observation result is tabulated in Table 2.

Example 2-2

Formic acid and lithium chloride (LiCl) were mixed and then heated to form a mixing liquid (95 wt % of the formic acid and 5 wt % of the lithium chloride). Avicel® cellulose (Avicel-pH-105-27NI, commercially available from Sigma Company) was added into the mixing liquid to form a mixture with 5 wt % of the Avicel® cellulose. The mixture stood at 70° C. for 12 hours to test its solubility. The cellulose solubility was observed by a polarizing microscope, and the observation result is tabulated in Table 2.

Example 2-3

Formic acid and sodium chloride (NaCl) were mixed and then heated to form a mixing liquid (a saturated solution of 90 wt % of the formic acid and 10 wt % of the sodium chloride). Avicel® cellulose (Avicel-pH-105-27NI, commercially available from Sigma Company) was added into the mixing liquid to form a mixture of 5 wt % of the Avicel® cellulose. The mixture stood at 70° C. for 19 hours to test its solubility. The cellulose solubility was observed by a polarizing microscope, and the observation result is tabulated in Table 2.

Example 2-4

Formic acid and lithium bromide (LiBr) were mixed and then heated to form a mixing liquid (90 wt % of the formic acid and 10 wt % of the lithium bromide). Avicel® cellulose (Avicel-pH-105-27NI, commercially available from Sigma Company) was added into the mixing liquid to form a mixture of 5 wt % of the Avicel® cellulose. The mixture stood at 70° C. for 0.5 hour to test its solubility. The cellulose solubility was observed by a polarizing microscope, and the observation result is tabulated in Table 2.

Example 2-5

Formic acid and sodium bromide (NaBr) were mixed and then heated to form a mixing liquid (82 wt % of the formic acid and 18 wt % of the sodium bromide). Avicel® cellulose (Avicel-pH-105-27NI, commercially available from Sigma Company) was added into the mixing liquid to form a mixture of 5 wt % of the Avicel® cellulose. The mixture stood at 70° C. for 9 hours to test its solubility. The cellulose solubility was observed by a polarizing microscope, and the observation result is tabulated in Table 2.

Example 2-6

Formic acid and calcium bromide ($CaBr_2$) were mixed and then heated to form a mixing liquid (88 wt % of the formic acid and 12 wt % of the calcium bromide). Avicel® cellulose (Avicel-pH-105-27NI, commercially available from Sigma Company) was added into the mixing liquid to form a mixture of 5 wt % of the Avicel® cellulose. The mixture stood at 70° C. for 6 hours to test its solubility. The cellulose solubility was observed by a polarizing microscope, and the observation result is tabulated in Table 2.

Example 2-7

Formic acid and barium bromide ($BaBr_2$) were mixed and then heated to form a mixing liquid (80 wt % of the formic acid and 20 wt % of the barium bromide). Avicel® cellulose (Avicel-pH-105-27NI, commercially available from Sigma Company) was added into the mixing liquid to form a mixture of 5 wt % of the Avicel® cellulose. The mixture stood at 70° C. for 6 hours to test its solubility. The cellulose solubility was observed by a polarizing microscope, and the observation result is tabulated in Table 2.

Example 2-8

Formic acid and magnesium chloride ($MgCl_2$) were mixed and then heated to form a mixing liquid (a saturated solution of 80 wt % of the formic acid and 20 wt % of the magnesium chloride). Avicel® cellulose (Avicel-pH-105-27NI, commercially available from Sigma Company) was added into the mixing liquid to form a mixture of 5 wt % of the Avicel® cellulose. The mixture stood at 65° C. for 2 hours to test its solubility. The cellulose solubility was observed by a polarizing microscope, and the observation result is tabulated in Table 2.

Example 2-9

Formic acid and magnesium chloride ($MgCl_2$) were mixed and then heated to form a mixing liquid (90 wt % of the formic acid and 10 wt % of the magnesium chloride). Avicel® cellulose (Avicel-pH-105-27NI, commercially available from Sigma Company) was added into the mixing liquid to form a mixture of 5 wt % of the Avicel® cellulose. The mixture stood at 70° C. for 12 hours to test its solubility. The cellulose solubility was observed by a polarizing microscope, and the observation result is tabulated in Table 2.

Example 2-10

Formic acid and calcium chloride ($CaCl_2$) were mixed and then heated to form a mixing liquid (a saturated solution of 75 wt % of the formic acid and 25 wt % of the calcium chloride). Avicel® cellulose (Avicel-pH-105-27NI, commercially available from Sigma Company) was added into the mixing liquid to form a mixture of 5 wt % of the Avicel® cellulose. The mixture stood at 65° C. for 1.5 hours to test its solubility. The cellulose solubility was observed by a polarizing microscope, and the observation result is tabulated in Table 2.

Example 2-11

Formic acid and calcium chloride ($CaCl_2$) were mixed and then heated to form a mixing liquid (82.5 wt % of the formic acid and 17.5 wt % of the calcium chloride). Avicel® cellulose (Avicel-pH-105-27NI, commercially available from Sigma Company) was added into the mixing liquid to form a mixture of 5 wt % of the Avicel® cellulose. The mixture stood at 70° C. for 2 hours to test its solubility. The cellulose solubility was observed by a polarizing microscope, and the observation result is tabulated in Table 2.

Example 2-12

Formic acid and calcium chloride ($CaCl_2$) were mixed and then heated to form a mixing liquid (88 wt % of the formic acid and 12 wt % of the calcium chloride). Avicel® cellulose (Avicel-pH-105-27NI, commercially available from Sigma Company) was added into the mixing liquid to form a mixture of 5 wt % of the Avicel® cellulose. The mixture stood at 70° C. for 6 hours to test its solubility. The cellulose solubility was observed by a polarizing microscope, and the observation result is tabulated in Table 2.

Example 2-13

Formic acid and calcium chloride ($CaCl_2$) were mixed and then heated to form a mixing liquid (90 wt % of the formic acid and 10 wt % of the calcium chloride). Avicel® cellulose (Avicel-pH-105-27NI, commercially available from Sigma Company) was added into the mixing liquid to form a mixture of 5 wt % of the Avicel® cellulose. The mixture stood at 70° C. for 12 hours to test its solubility. The cellulose solubility was observed by a polarizing microscope, and the observation result is tabulated in Table 2.

Example 2-14

Formic acid and barium chloride ($BaCl_2$) were mixed and then heated to form a mixing liquid (a saturated solution of 85 wt % of the formic acid and 15 wt % of the barium chloride). Avicel® cellulose (Avicel-pH-105-27NI, commercially available from Sigma Company) was added into the mixing liquid to form a mixture of 5 wt % of the Avicel® cellulose. The mixture stood at 70° C. for longer than 6 hours to test its solubility. The cellulose solubility was observed by a polarizing microscope, and the observation result is tabulated in Table 2.

Example 2-15

Formic acid and zinc chloride ($ZnCl_2$) were mixed and then heated to form a mixing liquid (60 wt % of the formic acid and 40 wt % of the zinc chloride). Avicel® cellulose (Avicel-pH-105-27NI, commercially available from Sigma Company) was added into the mixing liquid to form a mixture of 5 wt % of the Avicel® cellulose. The mixture stood at 50° C. for 0.25 hour to test its solubility. The cellulose solubility was observed by a polarizing microscope, and the observation result is tabulated in Table 2.

Example 2-16

Formic acid and zinc chloride ($ZnCl_2$) were mixed and then heated to form a mixing liquid (80 wt % of the formic acid and 20 wt % of the zinc chloride). Avicel® cellulose (Avicel-pH-105-27NI, commercially available from Sigma Company) was added into the mixing liquid to form a mixture of 5 wt % of the Avicel® cellulose. The mixture stood at 65° C. for 0.25 hour to test its solubility. The cellulose solubility was observed by a polarizing microscope, and the observation result is tabulated in Table 2.

Example 2-17

Formic acid and zinc chloride ($ZnCl_2$) were mixed and then heated to form a mixing liquid (95 wt % of the formic acid and 5 wt % of the zinc chloride). Avicel® cellulose (Avicel-pH-105-27NI, commercially available from Sigma Company) was added into the mixing liquid to form a mixture of 5 wt % of the Avicel® cellulose. The mixture stood at 70° C. for 6 hours to test its solubility. The cellulose solubility was observed by a polarizing microscope, and the observation result is tabulated in Table 2.

Example 2-18

Formic acid and zinc chloride ($ZnCl_2$) were mixed and then heated to form a mixing liquid (98 wt % of the formic acid and 2 wt % of the zinc chloride). Avicel® cellulose (Avicel-pH-105-27NI, commercially available from Sigma Company) was added into the mixing liquid to form a mixture of 5 wt % of the Avicel® cellulose. The mixture stood at 70° C. for longer than 6 hours to test its solubility. The cellulose solubility was observed by a polarizing microscope, and the observation result is tabulated in Table 2.

Example 2-19

Formic acid and iron chloride ($FeCl_3$) were mixed and then heated to form a mixing liquid (95 wt % of the formic acid and 5 wt % of the iron chloride). Avicel® cellulose (Avicel-pH-105-27NI, commercially available from Sigma Company) was added into the mixing liquid to form a mixture of 5 wt % of the Avicel® cellulose. The mixture stood at 70° C. for 1 hour to test its solubility. The cellulose solubility was observed by a polarizing microscope, and the observation result is tabulated in Table 2.

Example 2-20

Formic acid and iron chloride ($FeCl_3$) were mixed and then heated to form a mixing liquid (98 wt % of the formic acid and 2 wt % of the iron chloride). Avicel® cellulose (Avicel-pH-105-27NI, commercially available from Sigma Company) was added into the mixing liquid to form a mixture of 5 wt % of the Avicel® cellulose. The mixture stood at 70° C. for 3 hours to test its solubility. The cellulose solubility was observed by a polarizing microscope, and the observation result is tabulated in Table 2.

Example 2-21

Formic acid and iron chloride ($FeCl_3$) were mixed and then heated to form a mixing liquid (99 wt % of the formic acid and 1 wt % of the iron chloride). Avicel® cellulose (Avicel-pH-105-27NI, commercially available from Sigma Company) was added into the mixing liquid to form a mixture of 5 wt % of the Avicel® cellulose. The mixture stood at 70° C. for 6 hours to test its solubility. The cellulose solubility was observed by a polarizing microscope, and the observation result is tabulated in Table 2.

Example 2-22

Formic acid and ammonium chloride ($NH_4Cl$) were mixed and then heated to form a mixing liquid (a saturated solution of 90 wt % of the formic acid and 10 wt % of the ammonium chloride). Avicel® cellulose (Avicel-pH-105-27NI, commercially available from Sigma Company) was added into the mixing liquid to form a mixture of 5 wt % of the Avicel® cellulose. The mixture stood at 70° C. for longer than 12 hours to test its solubility. The cellulose solubility was observed by a polarizing microscope, and the observation result is tabulated in Table 2.

Example 2-23

Formic acid and aluminum chloride ($AlCl_3$) were mixed and then heated to form a mixing liquid (a saturated solution of 98 wt % of the formic acid and 2 wt % of the aluminum chloride). Avicel® cellulose (Avicel-pH-105-27NI, commercially available from Sigma Company) was added into the mixing liquid to form a mixture of 5 wt % of the Avicel® cellulose. The mixture stood at 70° C. for 6 hours to test its solubility. The cellulose solubility was observed by a polarizing microscope, and the observation result is tabulated in Table 2.

Example 2-24

Formic acid and tin chloride ($SnCl_3$) were mixed and then heated to form a mixing liquid (a saturated solution of 95 wt % of the formic acid and 5 wt % of the tin chloride). Avicel® cellulose (Avicel-pH-105-27NI, commercially available from Sigma Company) was added into the mixing liquid to form a mixture of 5 wt % of the Avicel® cellulose. The mixture stood at 70° C. for 6 hours to test its solubility. The cellulose solubility was observed by a polarizing microscope, and the observation result is tabulated in Table 2.

Example 2-25

Formic acid and calcium sulfate ($CaSO_4$) were mixed and then heated to form a mixing liquid (80 wt % of the formic acid and 20 wt % of the calcium sulfate). Avicel® cellulose (Avicel-pH-105-27NI, commercially available from Sigma Company) was added into the mixing liquid to form a mixture of 5 wt % of the Avicel® cellulose. The mixture stood at 70° C. for 6 hours to test its solubility. The cellulose solubility was observed by a polarizing microscope, and the observation result is tabulated in Table 2.

Example 2-26

Formic acid and heteropoly acid ($H_3PW_{12}O_{40}$) were mixed and then heated to form a mixing liquid (99 wt % of the formic acid and 1 wt % of the heteropoly acid). Avicel® cellulose (Avicel-pH-105-27NI, commercially available from Sigma Company) was added into the mixing liquid to form a mixture of 5 wt % of the Avicel® cellulose. The mixture stood at 70° C. for 6 hours to test its solubility. The cellulose solubility was observed by a polarizing microscope, and the observation result is tabulated in Table 2.

TABLE 2

| Examples | Salt | wt % | Dissolving temperature (° C.) | Dissolving period (hour) | Cellulose solubility |
|---|---|---|---|---|---|
| 2-1 | LiCl | 10 | 70 | 6 | Completely soluble |
| 2-2 | | 5 | 70 | 12 | Insoluble |
| 2-3 | NaCl | 10, saturated solution | 70 | 19 | Insoluble |
| 2-4 | LiBr | 10 | 70 | 0.5 | Completely soluble |
| 2-5 | NaBr | 18 | 70 | 9 | Insoluble |
| 2-6 | $CaBr_2$ | 12 | 70 | 6 | Completely soluble |
| 2-7 | $BaBr_2$ | 20 | 70 | 6 | Insoluble |
| 2-8 | $MgCl_2$ | 20, saturated solution | 65 | 2 | Completely soluble |
| 2-9 | | 10 | 70 | 12 | Insoluble |
| 2-10 | $CaCl_2$ | 25, saturated solution | 65 | 1.5 | Completely soluble |
| 2-11 | | 17.5 | 70 | 2 | Completely soluble |
| 2-12 | | 12 | 70 | 6 | Completely soluble |
| 2-13 | | 10 | 70 | 12 | Insoluble |
| 2-14 | $BaCl_2$ | 15, saturated solution | 70 | >6 | Insoluble |
| 2-15 | $ZnCl_2$ | 40 | 50 | 0.25 | Completely soluble |
| 2-16 | | 20 | 65 | 0.25 | Completely soluble |
| 2-17 | | 5 | 70 | 6 | Completely soluble |
| 2-18 | | 2 | 70 | >6 | Insoluble |
| 2-19 | $FeCl_3$ | 5 | 70 | 1 | Completely soluble |
| 2-20 | | 2 | 70 | 3 | Completely soluble |
| 2-21 | | 1 | 70 | 6 | Completely soluble |
| 2-22 | $NH_4Cl$ | 10, saturated solution | 70 | >12 | Insoluble |
| 2-23 | $AlCl_3$ | 2, saturated solution | 70 | 6 | Insoluble |
| 2-24 | $SnCl_3$ | 5, saturated solution | 70 | 6 | Insoluble |
| 2-25 | $CaSO_4$ | 20 | 70 | 6 | Insoluble |
| 2-26 | Heteropoly acid ($H_3PW_{12}O_{40}$) | 1 | 70 | 6 | Completely soluble |

Example 3-1

Formic acid and magnesium chloride ($MgCl_2$) were mixed, stirred, and heated to 70° C. under 1 atm to form a mixing liquid (80 wt % of the formic acid and 20 wt % of the magnesium chloride). Avicel® cellulose (Avicel-pH-105-27NI, commercially available from Sigma Company) was added into the mixing liquid to be dissolved at 70° C. for 2 hours. After the cellulose was completely dissolved, 0.5 parts by weight of water was added into 1 part of the solution with 5 wt % of the Avicel® cellulose. The solution was then heated to 100° C. and remained at 100° C. for 120 minutes to hydrolyze the cellulose. Thereafter, the hydrolyzed solution was neutralized by a saturated solution of sodium carbonate ($Na_2CO_3$), and precipitation of magnesium carbonate ($MgCO_3$) was removed. A total weight of a reducing carbohydrate of the hydrolysis was measured by 3,5-dinitrosalicylic acid (DNS method). The reducing carbohydrate yield (a ratio of the total weight of the reducing carbohydrate to the cellulose weight) was then calculated as shown in Table 3.

Example 3-2

Formic acid and magnesium chloride ($MgCl_2$) were mixed, stirred, and heated to 70° C. under 1 atm to form a mixing liquid (90 wt % of the formic acid and 10 wt % of the magnesium chloride). Avicel® cellulose (Avicel-pH-105-27NI, commercially available from Sigma Company) was added into the mixing liquid to be dissolved at 70° C. for 6 hours. After the cellulose was completely dissolved, 0.5 parts by weight of water was added into 1 part of the solution with 5 wt % of the Avicel® cellulose. The solution was then heated to 100° C. and remained at 100° C. for 120 minutes to hydrolyze the cellulose. Thereafter, the hydrolyzed solution was neutralized by a saturated solution of sodium carbonate ($Na_2CO_3$), and precipitation of magnesium carbonate ($MgCO_3$) was removed. A total weight of a reducing carbohydrate of the hydrolysis was measured by 3,5-dinitrosalicylic acid (DNS method). The reducing carbohydrate yield (a ratio of the total weight of the reducing carbohydrate to the cellulose weight) was then calculated as shown in Table 3.

TABLE 3

| Examples | Cellulose (wt %) | Mixing liquid ($MgCl_2$:formic acid) (wt %) | Dissolving temperature (° C.) | Dissolving period (hour) | Hydrolysis temperature (° C.) | Hydrolysis period (minutes) | Reducing carbohydrate yield (%) |
|---|---|---|---|---|---|---|---|
| 3-1 | 5 | 20:80 | 70 | 2 | 100 | 120 | 97.9 |
| 3-2 | 5 | 10:90 | 70 | 6 | 100 | 120 | 75.3 |

Example 4-1

Formic acid and calcium chloride (CaCl$_2$) were mixed, stirred, and heated to 50° C. under 1 atm to form a mixing liquid (85 wt % of the formic acid and 15 wt % of the calcium chloride). Avicel® cellulose (Avicel-pH-105-27NI, commercially available from Sigma Company) was added into the mixing liquid to be dissolved at 50° C. for 4 hours. After the cellulose was completely dissolved, 0.5 parts by weight of water was added into 1 part of the solution with 5 wt % of the Avicel® cellulose. The solution was then heated to 100° C. and remained at 100° C. for 60 minutes to hydrolyze the cellulose. Thereafter, the hydrolyzed solution was neutralized by a saturated solution of sodium carbonate (Na$_2$CO$_3$), and precipitation of calcium carbonate (CaCO$_3$) was removed. A total weight of a reducing carbohydrate of the hydrolysis was measured by 3,5-dinitrosalicylic acid (DNS method). The reducing carbohydrate yield (a ratio of the total weight of the reducing carbohydrate to the cellulose weight) was then calculated as shown in Table 4.

Example 4-2

Formic acid and calcium chloride (CaCl$_2$) were mixed, stirred, and heated to 70° C. under 1 atm to form a mixing liquid (88 wt % of the formic acid and 12 wt % of the calcium chloride). Avicel® cellulose (Avicel-pH-105-27NI, commercially available from Sigma Company) was added into the mixing liquid to be dissolved at 70° C. for 4 hours. After the cellulose was completely dissolved, 0.5 parts by weight of water was added into 1 part of the solution with 5 wt % of the Avicel® cellulose. The solution was then heated to 100° C. and remained at 100° C. for 60 minutes to hydrolyze the cellulose. Thereafter, the hydrolyzed solution was neutralized by a saturated solution of sodium carbonate (Na$_2$CO$_3$), and precipitation of calcium carbonate (CaCO$_3$) was removed. A total weight of a reducing carbohydrate of the hydrolysis was measured by 3,5-dinitrosalicylic acid (DNS method). The reducing carbohydrate yield (a ratio of the total weight of the reducing carbohydrate to the cellulose weight) was then calculated as shown in Table 4.

Example 4-3

Formic acid and calcium chloride (CaCl$_2$) were mixed, stirred, and heated to 90° C. under 1 atm to form a mixing liquid (90 wt % of the formic acid and 10 wt % of the calcium chloride). Avicel® cellulose (Avicel-pH-105-27NI, commercially available from Sigma Company) was added into the mixing liquid to be dissolved at 90° C. for 4 hours. After the cellulose was completely dissolved, 0.5 parts by weight of water was added into 1 part of the solution with 5 wt % of the Avicel® cellulose. The solution was then heated to 100° C. and remained at 100° C. for 60 minutes to hydrolyze the cellulose. Thereafter, the hydrolyzed solution was neutralized by a saturated solution of sodium carbonate (Na$_2$CO$_3$), and precipitation of calcium carbonate (CaCO$_3$) was removed. A total weight of a reducing carbohydrate of the hydrolysis was measured by 3,5-dinitrosalicylic acid (DNS method). The reducing carbohydrate yield (a ratio of the total weight of the reducing carbohydrate to the cellulose weight) was then calculated as shown in Table 4.

TABLE 4

| Examples | Cellulose (wt %) | Mixing liquid (CaCl$_2$:formic acid) (wt %) | Dissolving temperature (° C.) | Dissolving period (hour) | Hydrolysis temperature (° C.) | Hydrolysis period (minutes) | Reducing carbohydrate yield (%) |
|---|---|---|---|---|---|---|---|
| 4-1 | 5 | 15:85 | 50 | 4 | 100 | 60 | 78.4 |
| 4-2 | 5 | 12:88 | 70 | 4 | 100 | 60 | 70.6 |
| 4-3 | 5 | 10:90 | 90 | 4 | 100 | 60 | 67.3 |

Example 5-1

Formic acid and zinc chloride (ZnCl$_2$) were mixed, stirred, and heated to 50° C. under 1 atm to form a mixing liquid (60 wt % of the formic acid and 40 wt % of the zinc chloride). Avicel® cellulose (Avicel-pH-105-27NI, commercially available from Sigma Company) was added into the mixing liquid to be dissolved at 50° C. After the cellulose was completely dissolved, 0.5 parts by weight of water was added into 1 part of the solution with 5 wt % of the Avicel® cellulose. The solution was then heated to 100° C. and remained at 100° C. for 30 minutes to hydrolyze the cellulose. Thereafter, the hydrolyzed solution was neutralized by a saturated solution of sodium carbonate (Na$_2$CO$_3$), and precipitation of zinc carbonate (ZnCO$_3$) was removed. A total weight of a reducing carbohydrate of the hydrolysis was measured by 3,5-dinitrosalicylic acid (DNS method). The reducing carbohydrate yield (a ratio of the total weight of the reducing carbohydrate to the cellulose weight) was then calculated as shown in Table 5.

Example 5-2

Formic acid and zinc chloride (ZnCl$_2$) were mixed, stirred, and heated to 50° C. under 1 atm to form a mixing liquid (60 wt % of the formic acid and 40 wt % of the zinc chloride). Avicel® cellulose (Avicel-pH-105-27NI, commercially available from Sigma Company) was added into the mixing liquid to be dissolved at 50° C. After the cellulose was completely dissolved, 0.5 parts by weight of water was added into 1 part of the solution with 5 wt % of the Avicel® cellulose. The solution was then heated to 100° C. and remained at 100° C. for 45 minutes to hydrolyze the cellulose. Thereafter, the hydrolyzed solution was neutralized by a saturated solution of sodium carbonate (Na$_2$CO$_3$), and precipitation of zinc carbonate (ZnCO$_3$) was removed. A total weight of a reducing carbohydrate of the hydrolysis was measured by 3,5-dinitrosalicylic acid (DNS method). The reducing carbohydrate yield (a ratio of the total weight of the reducing carbohydrate to the cellulose weight) was then calculated as shown in Table 5.

TABLE 5

| Examples | Cellulose (wt %) | Water amount (wt %) | Hydrolysis period (minutes) | Reducing carbohydrate yield (%) |
|---|---|---|---|---|
| 5-1 | 5 | 50 | 30 | 65 |
| 5-2 | 5 | 50 | 45 | 89 |

Example 6

Formic acid and zinc chloride ($ZnCl_2$) were mixed, stirred, and heated to 55° C. under 1 atm to form a mixing liquid (60 wt % of the formic acid and 40 wt % of the zinc chloride). Dried sugar cane bagasse (43.58 wt % of glucan, 24.02 wt % of xylan, 12.45 wt % of acid soluble lignin, 18.12 wt % of acid insoluble lignin, and 1.71 wt % of ash) was added into the mixing liquid to be dissolved at 55° C. After the sugar cane bagasse was completely dissolved, 0.5 parts by weight of water was added into 1 part of the solution with 5 wt % of the sugar cane bagasse. The solution was then heated to 100° C. and remained at 100° C. for 120 minutes to hydrolyze the sugar cane bagasse. Thereafter, the hydrolyzed solution was neutralized by a saturated solution of sodium carbonate ($Na_2CO_3$), and precipitation of zinc carbonate ($ZnCO_3$) was removed. A glucose yield and a xylose yield of the hydrolysis were analyzed by high-performance liquid chromatography (HPLC), respectively. A total weight of a reducing carbohydrate of the hydrolysis was measured by 3,5-dinitrosalicylic acid (DNS method). The reducing carbohydrate yield was then calculated. The glucose yield is a ratio of moles of glucose product to moles of glucose monomer contained in the cellulose of the sugar cane bagasse. The xylose yield means a ratio of moles of the xylose production to moles of the xylose monomer contained in the hemicellulose of the sugar cane bagasse. The reducing carbohydrate yield is a ratio of the total weight of the reducing carbohydrate to the total weight of the cellulose and the hemicellulose in the sugar cane bagasse. The glucose yield, the xylose yield, and the reducing carbohydrate yield are tabulated in Table 6. After the hydrolysis, the hydrolyzed solution included 25.3 wt % of the zinc chloride, 33.2 wt % of the water, 38.2 wt % of the formic acid, 2.3 wt % of the reducing carbohydrate (wherein the glucose occupied 43.2 wt % of the reducing carbohydrate, and the xylose occupied 30.4 wt % of the reducing carbohydrate), 0.4 wt % of the acid soluble lignin, and 0.6 wt % of the acid insoluble lignin.

TABLE 6

| Examples | Sugar cane bagasse (wt %) | Water amount (wt %) | Hydrolysis period (minutes) | Glucose yield (%) | Xylose yield (%) | Reducing carbohydrate yield (%) |
|---|---|---|---|---|---|---|
| 6-1 | 5 | 50 | 30 | 36.3 | 88.5 | 93.3 |
| 6-2 | 5 | 50 | 60 | 53.3 | 94.2 | 97.9 |
| 6-3 | 5 | 50 | 120 | 70.4 | 89.9 | 105.2 |

Example 7

Formic acid and magnesium chloride ($MgCl_2$) were mixed, stirred, and heated to 50° C. under 1 atm to form a mixing liquid (80 wt % of the formic acid and 20 wt % of the magnesium chloride). Avicel® cellulose (Avicel-pH-105-27NI, commercially available from Sigma Company) was added into the mixing liquid to be dissolved at 50° C. for 2.5 hours. After the cellulose was completely dissolved, 0.5 parts by weight of water was added into 1 part of the solution with 5 wt % of the Avicel® cellulose. The solution was then heated to 100° C. and remained at 100° C. for 90 minutes to hydrolyze the cellulose. Thereafter, the hydrolyzed solution was neutralized by a saturated solution of sodium carbonate ($Na_2CO_3$), and precipitation of magnesium carbonate ($MgCO_3$) was removed. A total weight of a reducing carbohydrate of the hydrolysis was measured by 3,5-dinitrosalicylic acid (DNS method). The reducing carbohydrate yield (a ratio of the total weight of the reducing carbohydrate to the cellulose weight) was then calculated as shown in Table 7.

TABLE 7

| Example | Cellulose (wt %) | Mixing liquid ($MgCl_2$:formic acid) (wt %) | Dissolving temperature (° C.) | Dissolving period (hour) | Hydrolysis temperature (° C.) | Hydrolysis period (minutes) | Reducing carbohydrate yield (%) |
|---|---|---|---|---|---|---|---|
| 7 | 5 | 20:80 | 50 | 2.5 | 100 | 0 | 46 |
|   |   |       |    |     | 100 | 90 | 89 |

Example 8

Formic acid and zinc chloride ($ZnCl_2$) were mixed, stirred, and heated to 55° C. under 1 atm to form a mixing liquid (60 wt % of the formic acid and 40 wt % of the zinc chloride). Dried corn stalks (44.5 wt % of glucan, 12.4 wt % of xylan, 4.6 wt % of acid soluble lignin, 24.4 wt % of acid insoluble lignin, 2.7 wt % of water, and 3.8 wt % of ash) were added into the mixing liquid to be dissolved at 55° C. After the corn stalks were completely dissolved, 0.5 parts by weight of water was added into 1 part of the solution with 5 wt % of the corn stalks. The solution was then heated to 100° C. and remained at 100° C. for 90 minutes to hydrolyze the corn stalks. Thereafter, the hydrolyzed solution was neutralized by a saturated solution of sodium carbonate ($Na_2CO_3$), and precipitation of zinc carbonate ($ZnCO_3$) was removed. A glucose yield of the hydrolysis was analyzed by high-performance liquid chromatography (HPLC). A total weight of a reducing carbohydrate of the hydrolysis was measured by 3,5-dinitrosalicylic acid (DNS method). The reducing carbohydrate yield was then calculated. The glucose yield means a ratio of mole of glucose product to mole of glucose monomer contained in the cellulose of the corn stalks. The reducing carbohydrate yield means a ratio of the total weight of the reducing carbohydrate to the total weight of the cellulose and the hemicellulose in the corn stalks. The glucose yield and the reducing carbohydrate yield are tabulated in Table 8.

TABLE 8

| Example | Corn stalks (wt %) | Water amount (wt %) | Hydrolysis period (minutes) | Glucose yield (%) | Reducing carbohydrate yield (%) |
|---|---|---|---|---|---|
| 8 | 5 | 50 | 90 | 85 | 96 |

Example 9-1

Hydrochloric acid (with a concentration of 37 wt %), zinc chloride ($ZnCl_2$), and formic acid were mixed, stirred, and heated to 55° C. under 1 atm to form a mixing liquid (1 wt % of the hydrochloric acid, 5 wt % of the zinc chloride, and 94 wt % of the formic acid). Dried sugar cane bagasse (40.7 wt % of glucan, 20.5 wt % of xylan, 2.9 wt % of arabinan 27.4 wt % of lignin, 3.3 wt % of ash, and 5.2 wt % of others) was added into the mixing liquid to be dissolved at 65° C. After the sugar cane bagasse was completely dissolved, 0.5 parts by weight of water was added into 1 part of the solution with 10 wt % of the sugar cane bagasse. The solution was then heated to 100° C. to hydrolyze the sugar cane bagasse. Thereafter, the hydrolyzed solution was neutralized by a saturated solution of sodium carbonate ($Na_2CO_3$), and precipitation of zinc carbonate ($ZnCO_3$) was removed. A glucose yield and a xylose yield of the hydrolysis were analyzed by high-performance liquid chromatography (HPLC). A total weight of a reducing carbohydrate of the hydrolysis was measured by 3,5-dinitrosalicylic acid (DNS method). The reducing carbohydrate yield was then calculated. The glucose yield means a ratio of mole of glucose product to mole of glucose monomer contained in the cellulose of the sugar cane bagasse. The xylose yield is a ratio of moles of the xylose production to moles of the xylose monomer contained in the hemicellulose of the sugar cane bagasse. The reducing carbohydrate yield is a ratio of the total weight of the reducing carbohydrate to the total weight of the cellulose and the hemicellulose in the sugar cane bagasse. The glucose yield, the xylose yield, and the reducing carbohydrate yield are tabulated in Table 9.

Example 9-2

Hydrochloric acid (with a concentration of 37 wt %), iron chloride ($FeCl_3$), and formic acid were mixed, stirred, and heated to 55° C. under 1 atm to form a mixing liquid (1 wt % of the hydrochloric acid, 2 wt % of the iron chloride, and 97 wt % of the formic acid). Dried sugar cane bagasse (40.7 wt % of glucan, 20.5 wt % of xylan, 2.9 wt % of arabinan 27.4 wt % of lignin, 3.3 wt % of ash, and 5.2 wt % of others) was added into the mixing liquid to be dissolved at 65° C. After the sugar cane bagasse was completely dissolved, 0.5 parts by weight of water was added into 1 part of the solution with 10 wt % of the sugar cane bagasse. The solution was then heated to 100° C. to hydrolyze the sugar cane bagasse. Thereafter, the hydrolyzed solution was neutralized by a saturated solution of sodium carbonate ($Na_2CO_3$), and precipitation of iron carbonate ($Fe_2(CO_3)_3$) was removed. A glucose yield and a xylose yield of the hydrolysis were analyzed by high-performance liquid chromatography (HPLC). A total weight of a reducing carbohydrate of the hydrolysis was measured by 3,5-dinitrosalicylic acid (DNS method). The reducing carbohydrate yield was then calculated. The glucose yield means a ratio of mole of glucose product to mole of glucose monomer contained in the cellulose of the sugar cane bagasse. The xylose yield means a ratio of mole of the xylose production to mole of the xylose monomer contained in the hemicellulose of the sugar cane bagasse. The reducing carbohydrate yield means a ratio of the total weight of the reducing carbohydrate to the total weight of the cellulose and the hemicellulose in the sugar cane bagasse. The glucose yield, the xylose yield, and the reducing carbohydrate yield are tabulated in Table 9.

Example 9-3

Sulfuric acid (with a concentration of 98 wt %), iron chloride ($FeCl_3$), and formic acid were mixed, stirred, and heated to 55° C. under 1 atm to form a mixing liquid (1 wt % of the sulfuric acid, 2 wt % of the iron chloride, and 97 wt % of the formic acid). Dried sugar cane bagasse (40.7 wt % of glucan, 20.5 wt % of xylan, 2.9 wt % of arabinan 27.4 wt % of lignin, 3.3 wt % of ash, and 5.2 wt % of others) was added into the mixing liquid to be dissolved at 65° C. After the sugar cane bagasse was completely dissolved, 0.5 parts by weight of water was added into 1 part of the solution with 10 wt % of the sugar cane bagasse. The solution was then heated to 100° C. to hydrolyze the sugar cane bagasse. Thereafter, the hydrolyzed solution was neutralized by a saturated solution of sodium carbonate ($Na_2CO_3$), and precipitation of iron carbonate ($Fe_2(CO_3)_3$) was removed. A glucose yield and a xylose yield of the hydrolysis were analyzed by high-performance liquid chromatography (HPLC), respectively. A total weight of a reducing carbohydrate of the hydrolysis was measured by 3,5-dinitrosalicylic acid (DNS method). The reducing carbohydrate yield was then calculated. The glucose yield means a ratio of mole of glucose product to mole of glucose monomer contained in the cellulose of the sugar cane bagasse. The xylose yield means a ratio of mole of the xylose production to mole of the xylose monomer contained in the hemicellulose of the sugar cane bagasse. The reducing carbohydrate yield means a ratio of the total weight of the reducing carbohydrate to the total weight of the cellulose and the hemicellulose in the sugar cane bagasse. The glucose yield, the xylose yield, and the reducing carbohydrate yield are tabulated in Table 9.

TABLE 9

| Examples | Hydrolysis period (minutes) | Glucose yield (%) | Xylose yield (%) | Reducing carbohydrate yield (%) |
|---|---|---|---|---|
| 9-1 | 90 | 67.5 | 82.7 | 94.5 |
| 9-2 | 90 | 57.5 | 78.3 | 76.6 |
| 9-3 | 90 | 50.5 | 85.3 | 75.1 |

Example 10

Formic acid, hydrochloric acid or sulfuric acid, and metal salt were mixed and heated to form a mixing liquid. Avicel® cellulose (Avicel-pH-105-27NI, commercially available from Sigma Company) was added into the mixing liquid to test its solubility. The cellulose solubility was observed by a polarizing microscope, and the observation result is tabulated in Table 10. 1 wt % of the hydrochloric acid or the sulfuric acid added into the mixing liquid may accelerate dissolving the cellulose or reduce the metal salt concentration in the mixing liquid.

TABLE 10

| Examples | Metal salt (concentration) | Formic acid concentration | Acid catalyst (concentration) | Avicel cellulose (concentration) | Dissolving temperature (° C.) | Completely soluble period (hr) |
|---|---|---|---|---|---|---|
| 10-1 | $CaCl_2$ (5 wt %) | 94 wt % | HCl (1 wt %) | 5 wt % | 65 | 2.5 |
| 10-2 | $CaCl_2$ (12 wt %) | 88 wt % | none | 5 wt % | 70 | 6 |
| 10-3 | $MgCl_2$ (10 wt %) | 89 wt % | HCl (1 wt %) | 10 wt % | 65 | 1.5 |
| 10-4 | $MgCl_2$ (20 wt %) | 80 wt % | none | 5 wt % | 65 | 2 |
| 10-5 | $FeCl_3$ (2 wt %) | 97 wt % | $H_2SO_4$ (1 wt %) | 10 wt % | 70 | 2.5 |
| 10-6 | $FeCl_3$ (2 wt %) | 98 wt % | none | 5 wt % | 70 | 3 |
| 10-7 | $ZnCl_2$ (5 wt %) | 94 wt % | HCl (1 wt %) | 10 wt % | 65 | 1.5 |
| 10-8 | $ZnCl_2$ (5 wt %) | 95 wt % | none | 5 wt % | 70 | 6 |
| 10-9 | none | 99 wt % | $H_2SO_4$ (1 wt %) | 10 wt % | 65 | 6 |

Example 11

9.8 g of $ZnCl_2$, 5.10 g of hydrochloric acid, iron chloride ($FeCl_3$), and 174.2 g of formic acid were poured into a three-necked round bottom bottle (500 mL), and then stirred and heated. 21.0 g of sugar cane bagasse was added into the three-necked round bottom bottle. The mixture in the bottle was heated to 65° C. and remained at 65° C. for 3 hours to dissolve the sugar cane bagasse. After the sugar cane bagasse was completely dissolved, 0.5 parts by weight of water was added into 1 part of the solution with 10 wt % of the sugar cane bagasse. After the sugar cane bagasse was completely dissolved, 105.1 g of water was slowly and dropwise added into the solution in the bottle by a pipe. Thereafter, the solution in the bottle was heated to 100° C. and remained at 100° C. for 2 hours to hydrolyze the sugar cane bagasse. The reducing carbohydrate yield (a ratio of the weight of the reducing carbohydrate to the weight of the sugar cane bagasse) was 0.64.

Example 12

A simulation solution of a cellulose hydrolyzed by sulfuric acid and formic acid was prepared. The simulation solution included 3.2 wt % of glucose, 1.27 wt % of sulfuric acid, and 62.23 wt % of formic acid. 80 mL of the simulation solution was put into a rotary film evaporator at 45° C. and 20 mmHg to recycle 97% of the formic acid.

Example 13

Simulation solutions of a cellulose hydrolyzed by formic acid, hydrochloric acid, and/or calcium chloride were prepared, and the other experiment steps were similar to these of Example 12. The simulation solutions were put into a rotary film evaporator to recycle the formic acid, and recycle ratios of the formic acid are tabulated in Table 11.

TABLE 11

| | Evaporation and recycle of formic acid) | | | |
|---|---|---|---|---|
| Simulation solution composition | Example 12 | Example 13-1 | Example 13-2 | Example 13-3 |
| Sulfuric acid (%) | 1.27 | 0 | 0 | 0 |
| Hydrochloric acid (%) | 0 | 2.38 | 0 | 0.6 |
| Water content of hydrochloric acid (%) | 0 | 4.05 | 0 | 1.1 |
| Formic acid (%) | 62.23 | 57.07 | 50.8 | 58.7 |
| Calcium chloride (%) | 0 | 0 | 12.7 | 3.1 |
| Glucose (%) | 3.2 | 3.2 | 3.2 | 3.2 |
| Water (%) | 33.3 | 33.3 | 33.3 | 33.3 |
| Total (%) | 100 | 100 | 100 | 100 |
| Total acid concentration (M) | 17.23 | 16.32 | 13.80 | 16.17 |
| Total acid mole | 1.38 | 1.31 | 1.10 | 1.29 |
| Evaporation temperature (° C.) | 45 | 40 | 45 | 45 |
| Evaporation period (minute) | 30 | 30 | 10 | 30 |
| Distillate Proton molarity (M) | 16.8 | 15.8 | 16.2 | 16.4 |
| Proton mole | 1.3356 | 1.2482 | 1.053 | 1.1808 |
| Residue Proton molarity (M) | 10.6 | 6.6 | 6.4 | 4.6 |
| Proton mole | 0.053 | 0.0363 | 0.224 | 0.0391 |
| Recycle ratio | 0.97 | 0.96 | 0.95 | 0.91 |

Example 14

3.2 wt % of glucose, 12.7 wt % of $CaCl_2$, 50.8 wt % of formic acid, and 33.3 wt % of water were mixed to form an aqueous solution, wherein the formic acid concentration was 13.9M. Tributyl phosphate was diluted by n-octanol to a solution (with a concentration of 1M) serving as an extractant. 50 mL of the aqueous solution and 50 mL of the extractant were mixed to perform an extraction, and then stood to be separated into two layers. The extract phase liquid of the extraction was collected. The raffinate (remaining aqueous phase liquid of the extraction) was mixed with an equivalent volume of the extractant to perform another extraction, and then stood to be separated into two layers. The extract phase liquid of another extraction was collected and combined with the previous extract phase liquid. The above extraction was repeated 5 times, and the finally remaining aqueous phase liquid was 24 mL. The final remaining aqueous phase liquid was titrated by NaOH to calculate its proton molarity of 0.375M. The extraction ratio of the formic acid was calculated by the Formula: [(proton molarity of the aqueous solution)-(proton molarity of the final remaining aqueous phase solution)]/(proton molarity of the aqueous solution). In short, the extraction ratio of the formic acid was 98.7%.

Example 15

3.2 wt % of glucose, 12.7 wt % of $CaCl_2$, 50.8 wt % of formic acid, and 33.3 wt % of water were mixed to form an aqueous solution, wherein the formic acid concentration was 13.9M. Trioctyl amine was diluted by n-octanol to a solution (with a concentration of 1M) serving as an extractant. 50 mL of the aqueous solution and 50 mL of the extractant were mixed to perform an extraction, and then stood to be separated into two layers. The extract phase liquid of the extraction was collected. The raffinate (remaining aqueous phase liquid of the extraction) was analyzed for its formic acid concentration. The extraction ratio of the formic acid at one-time extraction by the trioctyl amine was 54.2%.

Example 16

44.4 wt % of formic acid, 11.2 wt % of $ZnCl_2$, 6.8 wt % of carbohydrate, 0.6 wt % of hydrochloric acid, and 37.0 wt % of water were mixed to form an aqueous solution. Diisobutyl ketone (DIBK) served as an extractant. 50 mL of the aqueous solution and 50 mL of the extractant were mixed to perform an extraction, and then stood to be separated into two layers. The extract phase liquid of the extraction was collected. The raffinate (remaining aqueous phase liquid of the extraction) was analyzed for its formic acid concentration. The extraction ratio of the formic acid at one-time extraction by the DIBK was 22%.

Example 17

44.4 wt % of formic acid, 11.2 wt % of $ZnCl_2$, 6.8 wt % of carbohydrate, 0.6 wt % of hydrochloric acid, and 37.0 wt % of water were mixed to form an aqueous solution. Di(2-ethylhexly) phosphoric acid (D2EHPA) served as an extractant. 50 mL of the aqueous solution and 50 mL of the extractant were mixed to perform an extraction, and then stood to be separated into two layers. The extract phase liquid of the extraction was collected. The raffinate (remaining aqueous phase liquid) of the extraction was analyzed for its formic acid concentration. The extraction ratio of the formic acid in one time extraction by the D2EHPA was 11%.

Example 18

7 parts by weight of tributyl phosphate (TBP) and 3 parts by weight of formic acid were dissolved in each other, and then heated to 90° C., 120° C., and 150° C., respectively, under 110 torr for 60 minutes, such that the recycle ratios of the formic acid were 42%, 66%, and 70%, respectively. The recycled formic acid had a concentration of 23M to 26M. The recycled formic acid could be reused in hydrolysis, and the recycled extractant TBP could be reused in formic acid extraction.

Example 19

7 parts by weight of trioctyl amine (TOA) and 3 parts by weight of formic acid were dissolved in each other, and then heated to 90° C., 120° C., and 150° C., respectively, under 110 torr for 60 minutes, such that the recycle ratios of the formic acid were 8%, 11%, and 80%, respectively. The recycled formic acid from the evaporation at 150° C. had a concentration of about 25M. The recycled formic acid could be reused in hydrolysis, and the recycled extractant TOA could be reused in formic acid extraction.

Example 20

10 parts by weight of sugar cane bagasse was added to 90 parts by weight of a mixing liquid (formic acid/zinc chloride/hydrochloric acid with a weight ratio of 94/5/1) to be heated and dissolved. 50 parts by weight of water and 100 parts by weight of the sugar cane bagasse solution were mixed and heated to perform a hydrolysis. The hydrolyzed solution was evaporated to be concentrated, wherein the concentrate and the hydrolyzed solution had a weight ratio of 37.2/100. The concentrate was filtered by a glass fiber filter with a pore size of 1 µm to remove solids therefrom. A soluble substance in the filtered cake was washed out by water. The remaining solids occupied 33.5 wt % of the sugar cane bagasse (solids/sugar cane bagasse), and occupied 5.5 wt % of the concentrate (solids/concentrate).

The filtrate from filtering the concentrate was mixed with an equivalent volume of tributyl phosphate (TBP) to extract the formic acid. An extract phase liquid and a raffinate phase liquid were filtered (by a glass fiber filter with a pore size of 1 µm), stood, and then separated. The above extraction steps were repeated 9 times, and solids of the extraction was separated by centrifuge or filtration. The solids were washed, baked, and weighted. The solids precipitated after the extraction occupied about 0.206 wt % of the concentrate before the extraction (precipitated solids/concentrate), occupied about 1.265 wt % of the sugar cane bagasse (precipitated solids/sugar cane bagasse). Total weight of the solids occupied 34.77 wt % of the sugar cane bagasse (total solids/sugar cane bagasse). The final raffinate phase liquid had a reducing carbohydrate concentration of 602 mg/mL with none formic acid detected.

Example 21

15 parts by weight of sugar cane bagasse was added to 85 parts by weight of a mixing liquid (formic acid/calcium chloride/hydrochloric acid with a weight ratio of 79/20/1) to be heated and dissolved. 50 parts by weight of water and 100 parts by weight of the sugar cane bagasse solution were mixed and heated to perform a hydrolysis. The hydrolyzed solution was filtered by a glass fiber filter with a pore size of 1 µm to remove solids therefrom. The filtrate from filtering the hydrolyzed solution had a reducing carbohydrate concentration of 64.5 mg/mL (5.2 wt %). The filtrate was mixed with an equivalent volume of tributyl phosphate (TBP) to extract the formic acid. An extract phase liquid and a raffinate phase liquid were filtered (by a glass fiber filter with a pore size of 1 µm), stood, and then separated. The raffinate phase liquid was mixed with an equivalent volume of tributyl phosphate (TBP), and stood to form another extract phase liquid and another raffinate phase liquid. Another extract phase liquid and another raffinate phase liquid were separated. The above extraction was repeated 7 times, and the final raffinate phase liquid had a reducing carbohydrate concentration of about 177 mg/mL (13.3 wt %) with non formic acid detected.

Example 22

160 g of cationic resin (Dowex-50wx4) was filled in a glass tube with a diameter of 2.5 cm and a length of 150 cm.

The cationic resin column was washed with a ZnCl$_2$ (10 mg/mL) of a flow rate of 1.5 mL/min. After protons (H$^+$) were completely exchanged with Zn$^{2+}$ ions, the redundant Zn$^{2+}$ ions were washed out by de-ionized water. As such, an ion exclusion chromatography separation column was completed. 5 mL of aqueous solution with 76 mg/mL of glucose and 154 mg/mL of ZnCl$_2$ were drop-wise added to the column. Subsequently, the column was washed by water with a flow rate of 1 mL/min, and fluid that flowed out of the column end was sampled to analyze the glucose concentration and the ZnCl$_2$ concentration, as shown in FIG. 1. At the effective separation point (about 85 mL of the fluid) of the glucose and the ZnCl2, the glucose purity might be greater than 85% (impurity less than 15%), and the recycle ratio of the glucose was 82.60%.

Example 23

Figure 2:
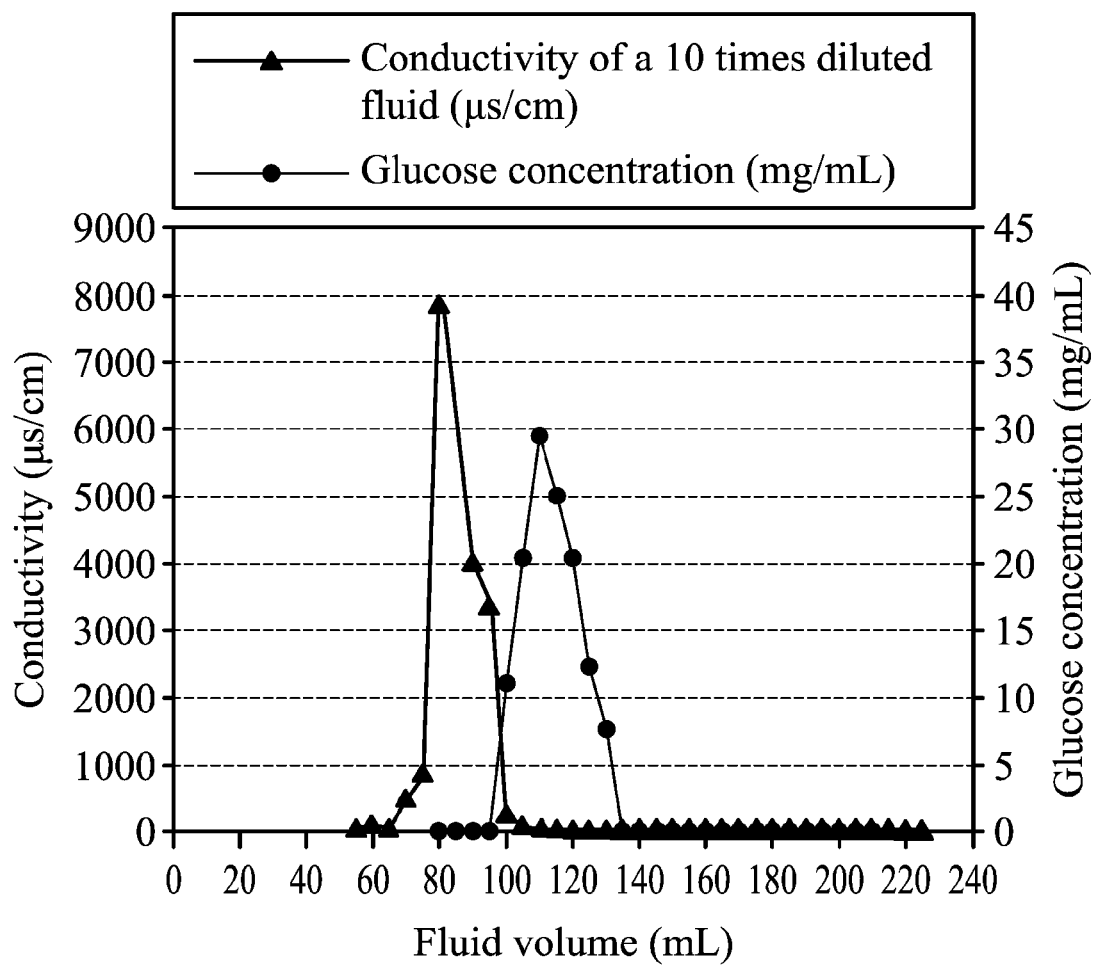
FIG. 2 shows curves of glucose concentration and conductivity versus fluid volume of a fluid that flowed out of a cationic resin for separating glucose in one embodiment of the disclosure.

160 g of cationic resin (UBK530) was filled in a glass tube with a diameter of 2.5 cm and a length of 150 cm. 5 mL of aqueous solution with 137 mg/mL of glucose and 140 mg/mL of ZnCl$_2$ were dropwise added to the column. Subsequently, the column was washed by water with a flow rate of 4 mL/min, and fluid that flowed out of the column end was sampled to analyze the glucose concentration and conductivity (relating to ionic substances), as shown in FIG. 2. At the effective separation point (about 105 mL of the fluid) of the glucose and the ions, the glucose purity might be greater than 85%, and the recycle ratio of the glucose was 82.5%.

Example 24

Figure 3:
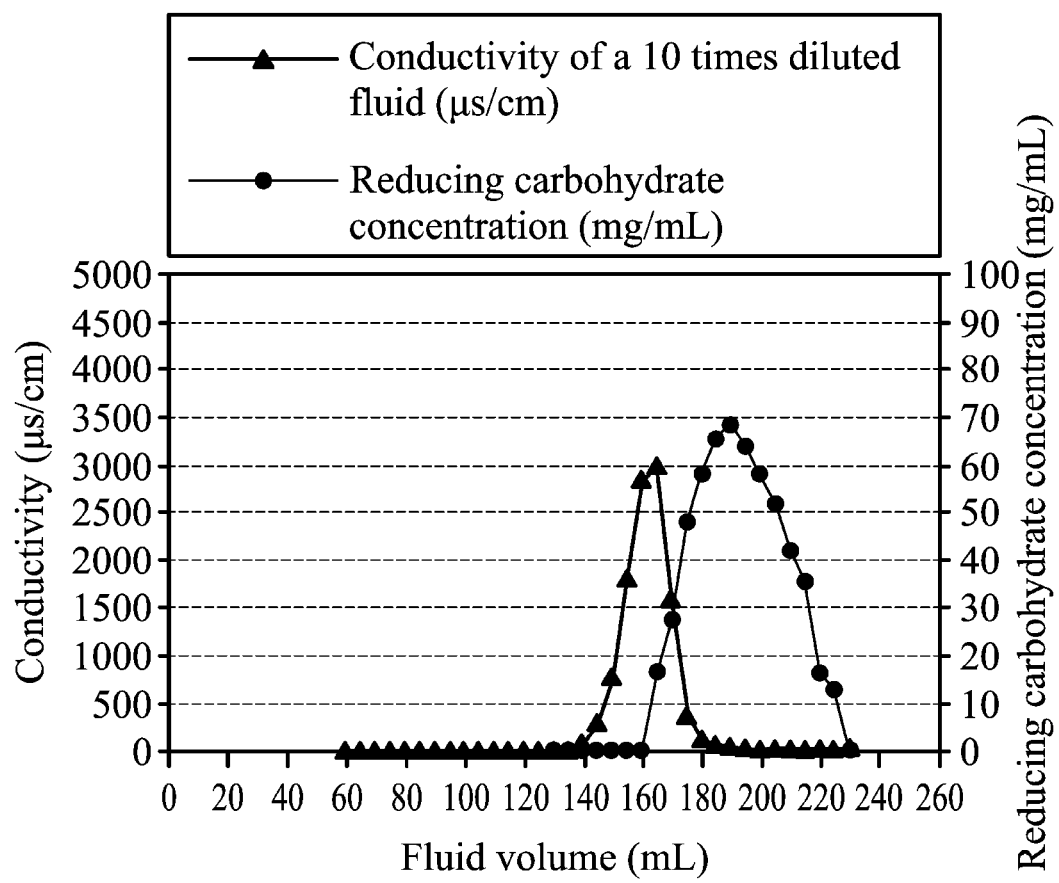
FIG. 3 shows curves of reducing carbohydrate concentration and conductivity versus fluid volume of a fluid that flowed out of a cationic resin for recycling reducing carbohydrate in one embodiment of the disclosure.

300 g of cationic resin (UBK555) was filled in a glass tube with a diameter of 2.5 cm and a length of 200 cm. 5 mL of the raffinate phase liquid in Example 20 with the reducing carbohydrate concentration of 602 mg/mL (46.3 wt %) was dropwise added to the column. Subsequently, the column was washed by water with a flow rate of 2.6 mL/min, and fluid that flowed out of the column end was sampled to analyze the reducing carbohydrate concentration and conductivity (relating to ionic substances), as shown in FIG. 3. At the effective separation point (about 175 mL of the fluid) of the reducing carbohydrate and the ions, the glucose purity might be greater than 85%, and the recycle ratio of the reducing carbohydrate was 86%.

Example 25

Figure 4:
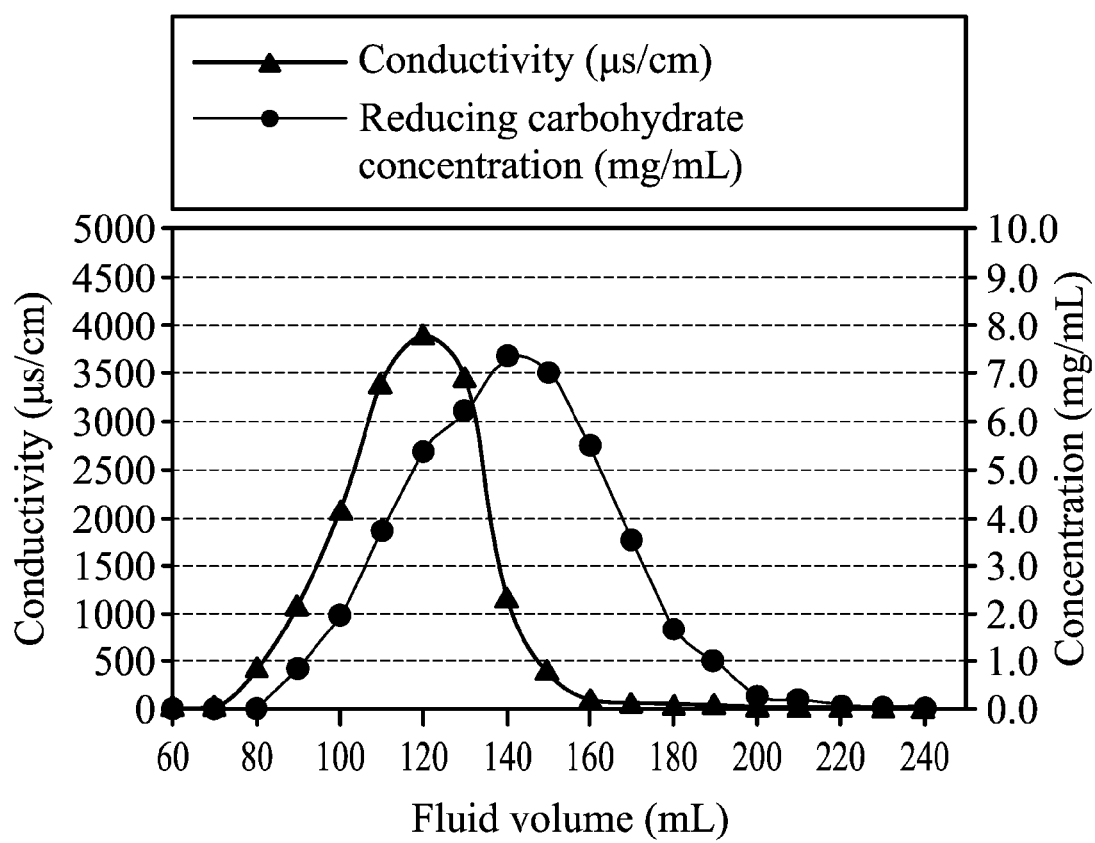
FIG. 4 shows curves of reducing carbohydrate concentration and conductivity versus fluid volume of a fluid that flowed out of a cationic resin for recycling reducing carbohydrate in one embodiment of the disclosure.

250 g of cationic resin (Dowex 99Ca) was filled in a glass tube with a diameter of 2.1 cm and a length of 200 cm. The raffinate phase liquid in Example 21 was neutralized to have a conductivity of 14.1 mS/cm and a reducing carbohydrate concentration of 90 mg/mL (6.9 wt %). 5 mL of the neutralized raffinate phase liquid was dropwise added to the column. Subsequently, the column was washed by water with a flow rate of 2.6 mL/min, and fluid that flowed out of the column end was sampled to analyze the reducing carbohydrate concentration and conductivity (relating to ionic substances), as shown in FIG. 4. At the effective separation point (about 130 mL of the fluid) of the reducing carbohydrate and the metal salt, the recycle ratio of the reducing carbohydrate was 73%.

Example 26

Figure 5:
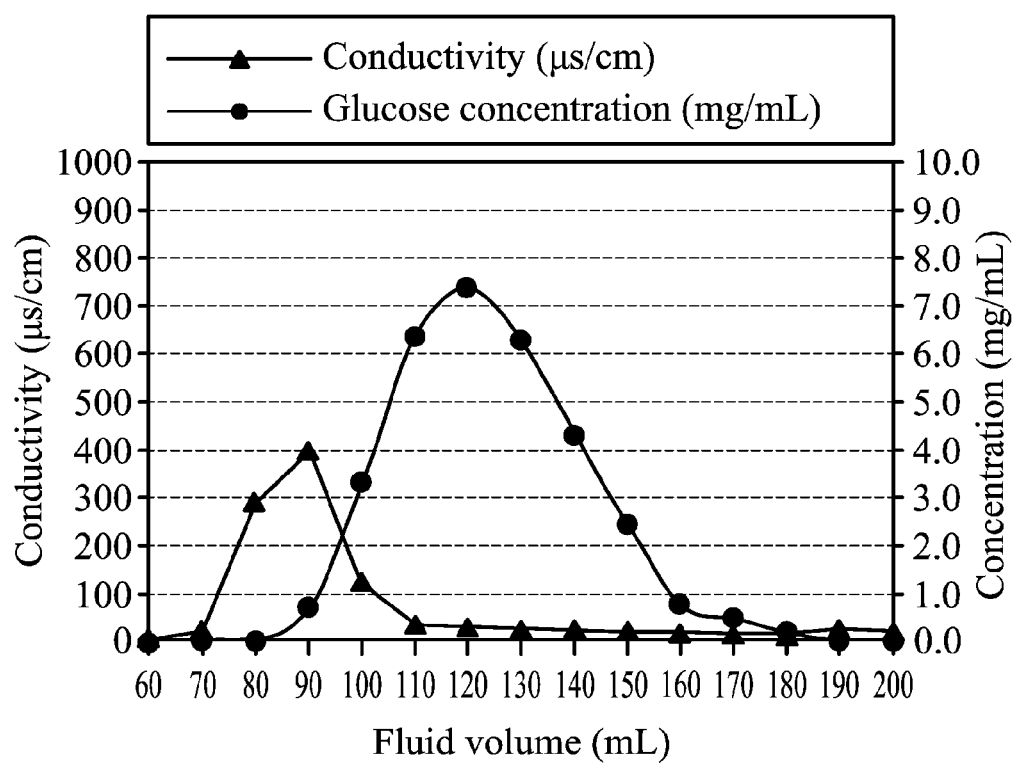
FIG. 5 shows curves of glucose concentration and conductivity versus fluid volume of a fluid that flowed out of a cationic resin for separating glucose and heteropoly acid in one embodiment of the disclosure.

Heteropoly acid (H$_3$PW$_{12}$O$_{40}$, commercially available from Aesar) and glucose were mixed to form a mixing liquid with 10 mg/mL of the heteropoly acid and 65 mg/mL of the glucose. 250 g of cationic resin (Dowex 99Ca) was filled in a glass tube with a diameter of 2.1 cm and a length of 200 cm. 5 mL of the mixing liquid was dropwise added to the column. Subsequently, the column was washed by water with a flow rate of 2.6mL/min, and fluid that flowed out of the column end was sampled to analyze the glucose concentration and conductivity (relating to ionic substances), as shown in FIG. 5. At the effective separation point (about 100 mL of the fluid) of the glucose and the heteropoly acid, the recycle ratio of the glucose was 98%.

Example 27

Different ratios of extractant TBP were added to an aqueous solution of formic acid (820 mg/mL), respectively. The mixtures were evaporated and condensed as shown in Table 12. The condensate liquid from the formic acid solution without any TBP had a formic acid concentration of 825 mg/mL. The condensate liquid from the formic acid solution added 11 wt % of the TBP had a formic acid concentration of 760 mg/mL. The condensate liquid from the formic acid solution added 20 wt % of the TBP had a formic acid concentration of 720 mg/mL. Accordingly, addition of the TBP helped to separate the formic acid and water, thereby increasing the formic acid concentration of remaining liquid after evaporation. In short, the extractant TBP was beneficial to concentrate the formic acid. In addition, the formic acid and the extractant TBP could be separated as shown in Example 18.

TABLE 12

| Examples | TBP additive amount | Formic acid concentration in the condensate liquid (mg/mL) |
| --- | --- | --- |
| 27-1 | 0 | 825 |
| 27-2 | 11 wt % | 760 |
| 27-3 | 19.3 wt % | 720 |

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. A method of separating carbohydrate, comprising:
   mixing (a) formic acid with (b) heteropoly acid, chloride or bromide of lithium, chloride of magnesium, bromide of calcium, chloride of iron, or combinations thereof to form a mixing liquid, wherein the mixing liquid consists of (a) formic acid and (b) heteropoly acid, chloride or bromide of lithium, chloride of magnesium, bromide of calcium, chloride of iron, or combinations thereof;
   dissolving a cellulose biomass in the mixing liquid at 40° C. to 90° C. to form a solution;
   mixing water and the solution to hydrolyze the cellulose biomass at 60° C. to 105° C. to form a carbohydrate solution;
   mixing an extractant and the carbohydrate solution to extract the formic acid out of the carbohydrate solution; and
   separating (b) heteropoly acid, the chloride or bromide of lithium, chloride of magnesium, bromide of calcium, chloride of iron, or combinations thereof out of the carbohydrate solution by an ion exclusion chromatography separation to obtain a carbohydrate, wherein i) when the mixing liquid includes the heteropoly acid, the heteropoly acid in the mixing liquid has a concentration of 1 wt % to 5 wt %;

ii) when the mixing liquid includes the chloride or bromide of lithium, the chloride or bromide of lithium in the mixing liquid has a concentration of 5 wt % to 20 wt %;

iii) when the mixing liquid includes the chloride of magnesium, the chloride of magnesium in the mixing liquid has a concentration of 10 wt % to 30 wt %;

iv) when the mixing liquid includes the bromide of calcium, the bromide of calcium in the mixing liquid has a concentration of 12 wt % to 40 wt %;

v) when the mixing liquid includes the chloride of iron, the chloride of iron in the mixing liquid has a concentration of 1 wt % to 10 wt %.

2. The method as claimed in claim 1, further comprising a step of distilling the carbohydrate solution to increase a carbohydrate concentration of the carbohydrate solution and to form a distillate.

3. The method as claimed in claim 2, wherein the step of distilling the carbohydrate solution is performed at a temperature of 40° C. to 60° C.

4. The method as claimed in claim 2, wherein the step of distilling the carbohydrate solution is performed under a pressure of 20 torr to 500 torr.

5. The method as claimed in claim 2, further comprising a step of mixing the distillate, the formic acid extracted out of the carbohydrate solution, and the extractant to form a mixture, and then heating the mixture to concentrate the formic acid.

6. The method as claimed in claim 5, wherein the step of heating the mixture is performed at a temperature of 50° C. to 105° C.

7. The method as claimed in claim 1, further comprising a step of removing solids in the carbohydrate solution by centrifuge and/or filtration.

8. The method as claimed in claim 1, wherein the step of mixing the extractant and the carbohydrate solution simultaneously precipitates precipitation.

9. The method as claimed in claim 8, further comprising a step of removing the precipitation by centrifuge and/or filtration.

10. The method as claimed in claim 1, wherein the step of separating (b) heteropoly acid, the chloride or bromide of lithium, chloride of magnesium, bromide of calcium, chloride of iron, or combinations thereof out of carbohydrate solution by an ion exclusion chromatography separation includes passing the carbohydrate solution through a cationic resin or an anionic resin.

11. The method as claimed in claim 10, further comprising a step of pre-exchanging cations in the cationic resin by a metal solution of lithium, magnesium, calcium, zinc, or iron.

12. The method as claimed in claim 10, further comprising a step of pre-exchanging anions in the anionic resin by a chloride or bromide solution.

13. The method as claimed in claim 1, wherein the cellulose biomass comprises lignocellulose, lignohemicellulose, or combinations thereof.

14. The method as claimed in claim 1, wherein the extractant comprises tributyl phosphate, tri-n-octylphosphine oxide, trioctyl amine, diisobutyl ketone, di(2-ethylhexly) phosphoric acid, or combinations thereof.

15. The method as claimed in claim 1, wherein the extractant and the carbohydrate solution have a volume ratio of 1:1 to 12:1.

16. The method as claimed in claim 1, further comprising a step of separating the extractant and the formic acid by distillation after the step of extracting the formic acid out of the carbohydrate solution.

17. The method as claimed in claim 16, wherein the distillation is performed under a pressure of 20 torr to 760 torr and a temperature of 40° C. to 200° C.

* * * * *